(12) United States Patent
Fischell et al.

(10) Patent No.: US 7,273,491 B2
(45) Date of Patent: Sep. 25, 2007

(54) MEANS AND METHOD FOR TREATING AN INTIMAL DISSECTION AFTER STENT IMPLANTATION

(75) Inventors: Robert E. Fischell, Dayton, MD (US); David R. Fischell, Fair Haven, NJ (US)

(73) Assignee: Cordis Corporation, Miami Lakes, FL (US)

( * ) Notice: Subject to any disclaimer, the term of this patent is extended or adjusted under 35 U.S.C. 154(b) by 699 days.

(21) Appl. No.: 10/158,099

(22) Filed: May 30, 2002

(65) Prior Publication Data
US 2003/0225417 A1    Dec. 4, 2003

(51) Int. Cl.
*A61F 2/06* (2006.01)

(52) U.S. Cl. ..................... 623/1.11; 606/108

(58) Field of Classification Search ............... 606/108, 606/191.199, 191, 192–199; 623/1, 1.11, 623/1.12; 604/22, 263, 264
See application file for complete search history.

(56) References Cited

U.S. PATENT DOCUMENTS 5,634,928 A * 6/1997 Fischell et al. ............ 623/1.11
5,891,154 A * 4/1999 Loeffler ..................... 623/1.11
6,159,195 A   12/2000 Ha et al.
6,221,090 B1 * 4/2001 Wilson ....................... 606/194

FOREIGN PATENT DOCUMENTS

WO      WO 93/13827 A1      7/1993

OTHER PUBLICATIONS

European Search Report, dated Oct. 2, 2003, for European Appln. No. EP 03 25 3351.

* cited by examiner

*Primary Examiner*—Michael J. Hayes
*Assistant Examiner*—Victor Nguyen

(57) ABSTRACT

The present invention is a "rescue" catheter that is designed to be placed over a fixed wire stent delivery catheter after angiography reveals that an intimal dissection has occurred typically as an edge dissection either just proximal or just distal to the stent.

4 Claims, 4 Drawing Sheets

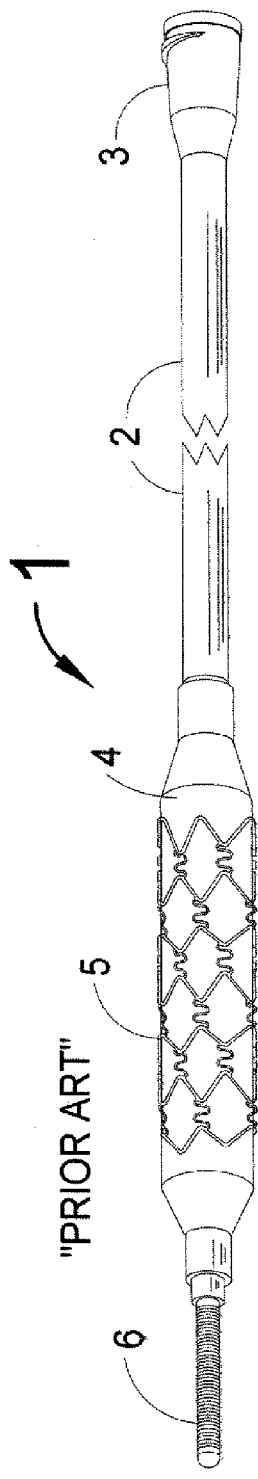
FIG. 1 "PRIOR ART"
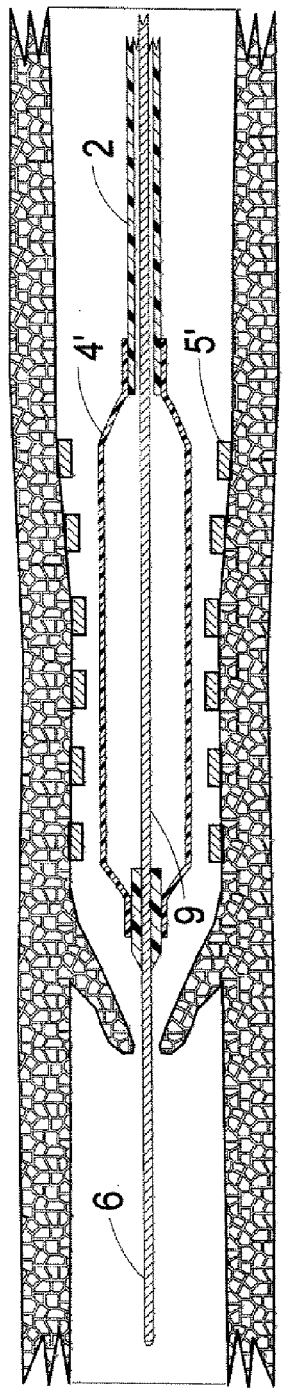
FIG. 2
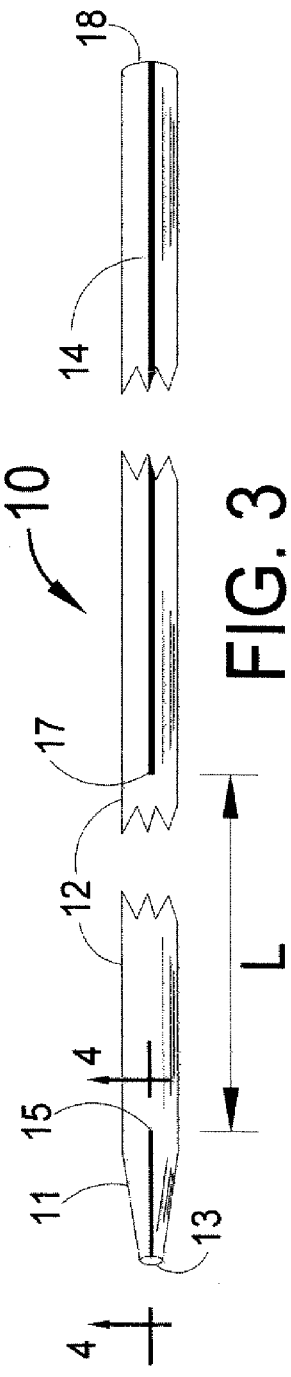
FIG. 3

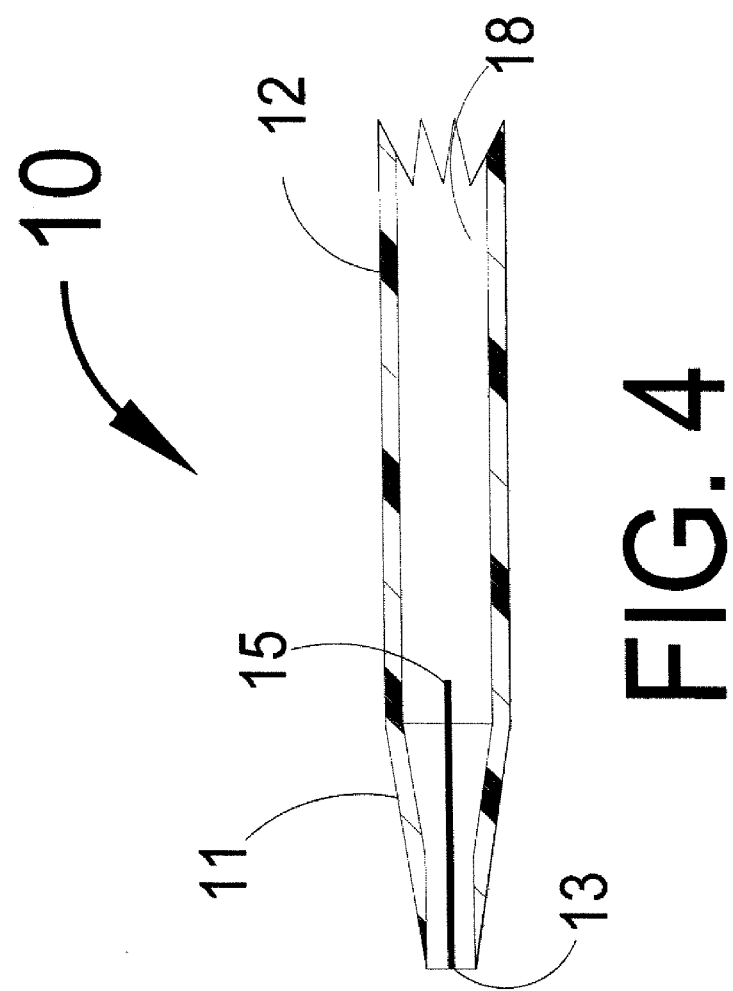

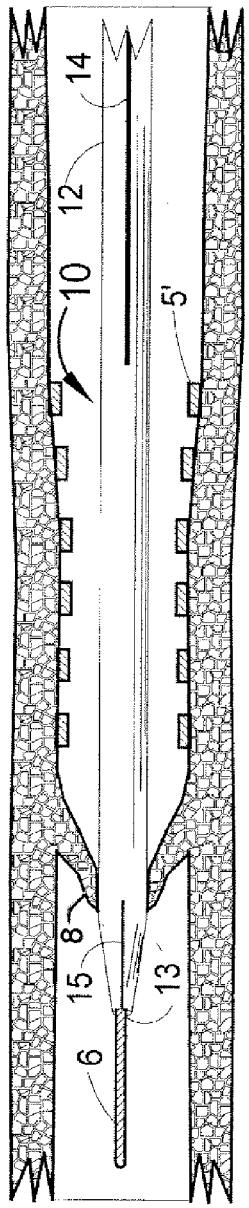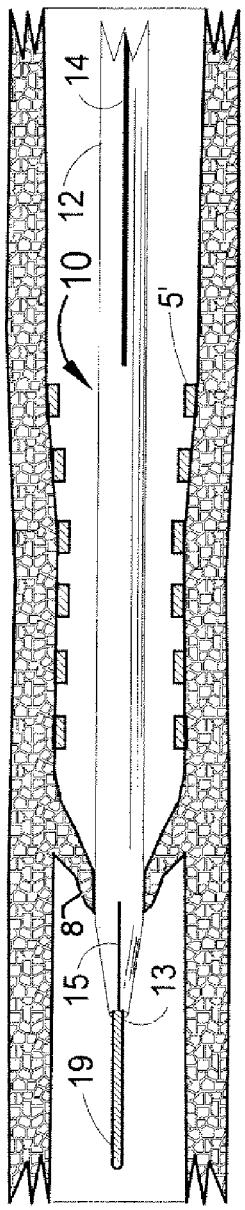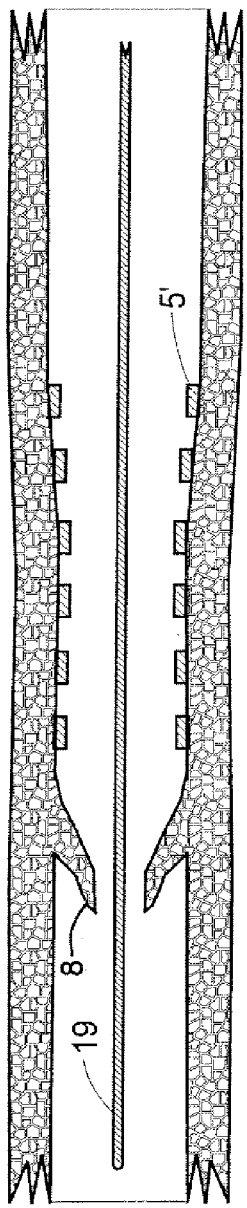

MEANS AND METHOD FOR TREATING AN INTIMAL DISSECTION AFTER STENT IMPLANTATION

FIELD OF USE

This invention is in the field of catheters that are used to treat an intimal dissection resulting from the placement of a stent into an artery such as a coronary artery.

BACKGROUND OF THE INVENTION

In U.S. patent Ser. No. 09/444,104, incorporated herein by reference, a stent delivery catheter is described that has a fixed guide wire at its distal end. Although this system for delivering a stent into a vessel of the human body has the advantage of providing an extremely small outside diameter for easy insertion through even the narrowest of arterial stenoses, it does have a potential difficulty in for those few cases when an intimal dissection occurs after stent implantation. Specifically, if a separate guide wire is used during stent implantation, it can be kept in place after the stent delivery catheter is removed thus allowing insertion of a second stent delivery system over the guide wire to repair any intimal dissection. However, if the guide wire is fixed to the stent delivery catheter, it will be removed with the stent delivery catheter after the stent has been delivered. Without a guide wire through that portion of the artery where an intimal dissection has occurred, it can be extremely difficult to place a second stent delivery catheter to deliver a second stent to repair such an intimal dissection.

SUMMARY OF THE INVENTION

The present invention is a "rescue" catheter that is designed to be placed over a fixed wire stent delivery catheter after angiography reveals that an intimal dissection has occurred typically as an edge dissection either just proximal or just distal to the stent. The present invention is also a method for using such a catheter to repair an intimal dissection. It should be understood that an intimal dissection that is in close proximity to the edge of an implanted stent is called an "edge dissection".

As previously stated, U.S. patent Ser. No. 09/444,104 describes a fixed guide wire stent delivery catheter with an extremely small outside diameter which can be used to deliver a stent through a very tight arterial stenosis. After the stent on the stent delivery catheter has been delivered into the arterial wall, the balloon would be deflated and the fixed guide wire stent delivery catheter would be left in place. Contrast medium would then be delivered to the site of the dilated stenosis to indicate if there is any arterial wall dissection. Such an intimal dissection would typically occur near the proximal or distal edge of the stent. In most cases, there will be no edge dissection, the stent delivery catheter would be removed from the body, and the stent implantation would be considered to be successfully completed.

If, however, angiography with the contrast medium indicates that an edge dissection has occurred, then a second stent must be placed at the site of the dissection to restore normal blood flow. If a dissection occurs, the fixed guide wire stent delivery catheter would be left in place with its balloon deflated. The Luer fitting at the proximal end of the stent delivery catheter would then be cut off and a rescue catheter would be advanced over the stent delivery catheter. The rescue catheter would be advanced until its distal end extended beyond the site of the edge dissection. The fixed wire stent delivery catheter would then be pulled out of the body through the rescue catheter, and a conventional guide wire would be inserted through the rescue catheter. The rescue catheter would then be removed leaving the guide wire in place. A conventional stent delivery catheter would then be used to deliver a second stent to the site of the intimal dissection at the edge of the first implanted stent, thus repairing the dissection.

Thus, an object of the present invention is a rescue catheter that is designed to be placed over a fixed guide wire stent delivery system if angiography indicates that an intimal dissection has occurred, the rescue catheter being designed for placement of a conventional guide wire through it so that a second stent delivery system can be advanced over the guide wire to deliver a stent to repair the intimal dissection.

Another object of the present invention is a method for using a rescue catheter to treat an intimal dissection created by the delivery of a stent from a fixed guide wire stent delivery system.

These and other important objects and advantages of this invention will become apparent from the detailed description of the invention and the associated drawings provided herein.

BRIEF DESCRIPTION OF THE DRAWINGS

FIG. 1 is a side view of a prior art fixed guide wire stent delivery system shown with the stent mounted onto the balloon.

FIG. 2 is a longitudinal cross section of the fixed guide wire stent delivery system with the stent shown delivered into an arterial stenosis, where the balloon is deflated and a distal intimal dissection has occurred.

FIG. 3 is a side view of the rescue catheter that is adapted to pass through an intimal dissection.

FIG. 4 is a longitudinal cross section of a distal portion of the rescue catheter at section 4-4 of FIG. 3.

FIG. 5 shows the rescue catheter placed over the fixed guide wire stent delivery system and through an intimal dissection.

FIG. 6 shows the rescue catheter in place with the stent delivery system removed and a conventional guide wire placed through the rescue catheter with its distal end placed beyond the intimal dissection.

FIG. 7 shows the guide wire in place and the rescue catheter removed.

DETAILED DESCRIPTION OF THE INVENTION

Figure 8:
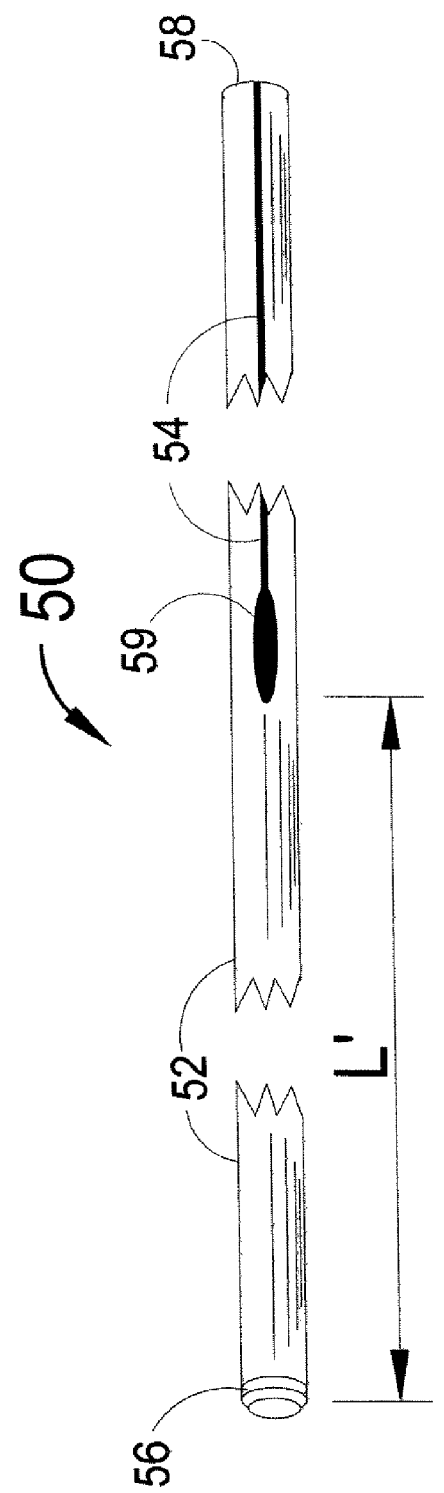
FIG. 8 is an alternate embodiment of the present invention having a cylindrical distal end and other optional features.

FIG. 1 is a side view of a prior art stent delivery system 1 having a fixed guide wire 6 attached to the distal end of a balloon 4 onto which a stent 5 has been mounted. A shaft 2 that extends for most of the length of the stent delivery system 1 is attached at its distal end to the balloon 4 and at its proximal end to a Luer fitting 3. (This type of stent delivery system is described in detail in U.S. Pat. No. 09/444,104 above.) If angiography indicates that there has been an intimal dissection after the stent 5 is placed into an arterial stenosis, the Luer fitting 3 is cut off from the shaft 2 so that a rescue catheter can be advanced over the stent delivery system 1.

FIG. 2 illustrates the delivered stent 5' deployed into an artery with a deflated balloon 4' attached at its distal end to the guide wire 6 and at its proximal end to the shaft 2. A core wire 9 attached to the fixed guide wire 6 could extend to the proximal end of the stent delivery system 1.

FIG. 3 is a side view of a rescue catheter 10 having a shaft 12 that extends for most of its length, an interior lumen 18 and a distal cone 11 located at a distal portion of the catheter 10. The shaft 12 has an elongated slit 14 whose distal end 17 is situated between 0.5 and 20 cm from the proximal end of the cone 11. The cone 11 has a distal opening 13 at its distal end and at least one slit 15 that begins at the distal opening 13 and extends to and possibly beyond the distal end of the cylindrical shaft 12. The length of the cone 11 should be less than 10 cm and optimally approximately one cm. The length of the cylindrical shaft 12 should be at least 100 cm and optimally longer than 125 cm. The inside diameter of the shaft 12 should be just slightly larger than the maximum outside diameter of the stent delivery system 1. The inside diameter of the distal opening 13 should optimally be slightly smaller than the shaft 2 in FIG. 1 of the fixed guide wire stent delivery system.

FIG. 4 is a longitudinal cross section of a distal portion of the catheter 10 showing the distal cone 11, the shaft 12, the distal opening 13, a slit 15 and the lumen 18. Although the slit 15 is shown extending into the shaft 12, it is envisioned that its proximal end could remain within the cone 11 or that it could extend for as much as a centimeter into the shaft 12. Furthermore, it should be understood that there could be as many as four slits 15 around the circumference of the cone 11 or as few as one.

FIGS. 5, 6 and 7 illustrate how the present invention would be used to place a conventional guide wire through an intimal dissection that extends beyond the edge of a stent. FIG. 5 shows the catheter 10 inside an artery into which the stent 5' has been deployed. If there is an intimal dissection 8 extending beyond the edge of the stent 5', it can be detected by the interventional cardiologist using contrast medium. After an intimal dissection is detected, the Luer fitting 3 is cut off from the shaft 2 of the stent delivery system 1. The interventional cardiologist would then open the cone 11 and place it over the cut off proximal end of the shaft 2 of the stent delivery system 1.

The interventional cardiologist would then advance the catheter 10 over the shaft 2 until the proximal end of the shaft 2 could be pulled out of the slit 14. While holding the proximal end of the shaft 2 in one hand, the interventional cardiologist would, with his other hand, advance the rescue catheter 10 over the stent delivery system 1 until the opening 13 of the cone 11 was advanced over the guide wire 6 and past beyond the intimal dissection 8. Because of its conical shape, and because the inside diameter of the end hole 13 would be approximately the same as the outside diameter of the guide wire 6, the distal end of the catheter 10 should readily pass through the dissection 8. Since it is expected that the diameter of the guide wire 6 would be 0.014 inches, an optimal diameter for the opening 13 of the cone 11 would be approximately 0.014 inches.

After the rescue catheter 10 is positioned as shown in FIG. 5, the stent delivery system 1 is pulled back out of the catheter 10 and out of the patient's body. A conventional guide wire 19 is then inserted through the catheter 10 until its distal end lies distal to the intimal dissection 8. This condition is shown in FIG. 6. The catheter 10 is then removed from the patient's body and the guide wire 19 remains in place as shown in FIG. 7. Having the slit 14 in the side of the shaft 12 allows a conventional 135 cm length of guide wire 19 to be used. Alternatively, a guide wire 19 that is longer than twice the length of the rescue catheter 10 could be used without utilizing the slit 14 of the catheter 10.

FIG. 8 is an alternative embodiment catheter 50 having a cylindrical distal end with radiopaque marker ring 56, a shaft 52 and a slit 54 that runs from a point a distance L' from the distal marker ring 56 to the proximal end 58 of the shaft 52. The distance L' is between 0.5 and 20 cm. An access hole 59 at the distal end of the slit 54 facilitates extraction of the proximal end of the fixed guide wire stent delivery system 1 of FIGS. 1 and 2 from the slit when the rescue catheter 50 is inserted into the patient's body. It is envisioned that a radiopaque marker ring 56 and an access hole 59 could also be used with the tapered end catheter of FIG. 3 where the radiopaque marker ring would be placed just proximal to the proximal end of the distal slit 15.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. In combination:
   a fixed guide wire stent delivery catheter; and
   a rescue catheter designed for placement over said fixed guide wire stent delivery catheter after an intimal dissection has been detected following the placement of a stent into an artery of a human body, the rescue catheter comprising:
   a distal portion that is a flexible, thin-walled cone having a length of less than 10 centimeters, the cone having a proximal end that is fixedly attached to the distal end of a cylindrical shaft that is at least 1 meter long, the cylindrical shaft having a longitudinal slit extending from its proximal end.

2. The combination of claim 1 wherein the cone at the distal portion of the rescue catheter has at least one longitudinal slit for most of the length of the cone, the slit having a proximal end and a distal end, the distal end being situated at a distal opening of the cone.

3. The combination of claim 1 wherein there is a distal opening at the distal end of the cone, the diameter of the distal opening being approximately 0.014 inches.

4. In combination:
   a fixed guide wire stent delivery catheter; and
   a rescue catheter designed for placement over said fixed guide wire stent delivery catheter after an intimal dissection has been detected following the placement of a stent into an artery of a human body;
   said rescue catheter designed for placement over the fixed guide wire stent delivery catheter, comprising:
   a flexible, thin-walled cylindrical shaft that is at least 1 meter long, the cylindrical shaft having an opening at its distal end and also having a longitudinal slit extending from its proximal end and extending for most of the length of the cylindrical shaft.

* * * * *